(12) United States Patent
Hobbs et al.

(10) Patent No.: US 6,465,196 B1
(45) Date of Patent: Oct. 15, 2002

(54) DRUG SCREEN FOR IDENTIFYING AN AGENT THAT MODULATES LOW DENSITY LIPOPROTEIN RECEPTOR ADAPTIN-LIGAND BINDING

(75) Inventors: Helen H. Hobbs, Dallas, TX (US); Christine K. Garcia, Dallas, TX (US); Robert I. Barnes, Frisco, TX (US); Jonathan Cohen, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/804,778

(22) Filed: Mar. 13, 2001

(51) Int. Cl.[7] .................. G01N 33/53; G01N 33/566; C12Q 1/68
(52) U.S. Cl. ..................... 435/7.1; 435/6; 436/501
(58) Field of Search ............. 435/7.1, 7.2; 530/350, 530/300; 436/501

(56) References Cited

U.S. PATENT DOCUMENTS 6,280,964 B1 * 8/2001 Kavanaugh et al. ......... 435/7.8
6,323,177 B1 * 11/2001 Curran et al. ................ 514/8

OTHER PUBLICATIONS

Gotthardt et al, Interactions of the low density lipoprotein receptor gene family with cytosolic adaptor and scaffold proteins suggest diverse biological functions in cellular communication and signal transduction, J. Biol. Chem. 275:25616–25624, 2000.*

Morris, S. M. and Cooper, J. A. Disabled–2 colocalizes with the LDLR in clathrin–coated pits and interacts with AP–2 Traffic 2:111–123, 2001.*

Trommsdorff et al, Interaction of cytosolic adaptor proteins with neuronal apolipoprotein E receptors and the amyloid precursor protein. J. Biol. Chem. 273: 33556–33560, 1998.*

* cited by examiner

*Primary Examiner*—Elizabeth Kemmerer
*Assistant Examiner*—Ruixiang Li
(74) *Attorney, Agent, or Firm*—Richard Aron Osman

(57) ABSTRACT

Low density lipoprotein receptor (LDRL) adaptin is a novel, key component of human cholesterol regulation, which provides a target for rational drug design and screening, therapeutic intervention, and diagnosis. Disclosed reagents include a variety of LDLR adaptin and LDLR adaptin PTB and CC domain compositions, including in vitro compositions comprising a natural human LDLR adaptin PTB domain and a ligand such as an NPXY (SEQ ID NO:7) peptide. These LDLR adaptin reagents are used, inter alia, in rational drug screening methods. The invention also provides polynucleotides encoding the subject LDLR adaptin polypeptides, including natural coding sequences, which may be used as probes or primers for detecting or amplifying LDLR adaptin genes and transcripts.

11 Claims, 6 Drawing Sheets

Fig. 2B

```
                                                                                        62
human    MDALKSAGRALIRSPSLAKQSWGGGGRHRKLPENWTDTRETLLEG-MLFSLKYLGMTLVEQPK
mouse    MDALKSAGRALIRSPSLAKQSWAGG-RHRKLPENWTDTRETLLEG-MVFSLKYLGMTLVERPK
Xenopus  MDALKSAGRAIIRSPSIAKQSWGG-KHKKLPENWTDTRETLLEG-MLFHKYLGMTLVEQPK 125
human    GEELSAAAIKRLVATAKASGKKLQKVTLKVSPRGIILTDNLTNQLIENVSIYRISYCTADKMH
mouse    GEELSAAAVKRLVATAKASGKKLQKVTLKVSPRGIILTDSLTSQLIENVSIYRISYCTADKMH
Xenopus  GEELSATAVKRLVATAKASGKKLQKVLLKVSPRGIILDXAXNQLIENVSIYRISYCTADKMH 188
human    DKVFAYIAQSQHNQSLECHAFLCTKRKMAQAVTLTVAQAFKVAFEFWQVSKEEKEKRDKASQE
mouse    DKVFAYIAQSQQNESLECHAFLCTKRKVAQAVTLTVAQAFKVAFEFWQVSKEEKEKREKANQE
Xenopus  DKVFAYIAQSQQNETLECHAFLCTKRKMAQAVTLTVAQAFKVAFEFWQVSRKRKRESLVHME 248
human    GGDVLGARQD--CTPPLKSLVATGNLLDLEETAKAPLSTVSANTTNMDEVPRPQALS-GSSVV
mouse    GGDVPGTRRD--STPSLKTLVATGNLLDLEEVAKAPLSTVSANTNNVDETPRPQVLG-NNSVV
Xenopus  KGQVVLSLMAPRVSPALKHQHLQ-TFWILEDCAKA-FDVLNASDNHIEEVLRQNASNENNNIV 308
human    WELDDGLDEAFSRLAQSRTNPQVLDTGLTAQDMHYAQCLSPVDWDKPDSSGTEQDD-LFSF
mouse    WELDDGLDEAFSRLAQSRTNPQVLDTGLSAQDIHYAQCLSPTDWDKPDSSGIDQDDDVFTF
Xenopus  WELDDGLDEAFARLAEXRTNPQVLDIGLTXNDLQSEECLSPTSWDKLELNPAEADE-LFME
```

US 6,465,196 B1

DRUG SCREEN FOR IDENTIFYING AN AGENT THAT MODULATES LOW DENSITY LIPOPROTEIN RECEPTOR ADAPTIN-LIGAND BINDING

The research carried out in the subject application was supported in part by grant No. POI HL20948 from the National Institutes of Health. The government may have rights in this invention.

FIELD OF THE INVENTION

The field of this invention is cholesterol regulation.

BACKGROUND OF THE INVENTION

Atherogenic low density lipoproteins are cleared from the circulation by low density lipoprotein receptors (LDLR) in the liver. Two inherited forms of hypercholesterolemia result from loss of hepatic LDLR activity: the autosomal dominant disorder, familial hypercholesterolemia (FH), caused by mutations in the LDLR gene, and autosomal recessive hypercholesterolemia (ARH) in which the LDLR gene is normal. We mapped the ARH locus to a ~1 centimorgan interval on chromosome 1p35 and identified six mutations in a gene encoding a new adaptor protein, LDLR adaptin, in 32 alleles from 16 unrelated ARH patients. LDLR adaptin contains a phosphotyrosine binding (PTB) domain, which binds NPXY (SEQ ID NO:7) motifs in the cytoplasmic tails of cell surface receptors, including the LDLR. Defects in LDLR adaptin result in selective impairment of LDLR function in the liver, whereas correction of LDLR adaptin defects and stabilization of LDLR adaptin function reduces associated hypercholesterolemia.

SUMMARY OF THE INVENTION

The invention provides methods and compositions relating to hypercholesterolemia. The inventors disclose a novel, key component of human cholesterol regulation, which provides a target for rational drug design and screening, therapeutic intervention, and diagnosis.

In particular embodiments, the invention provides a variety of LDLR adaptin and LDLR adaptin PTB and CC domain compositions, including compositions comprising a recombined natural human LDLR adaptin PTB or CC domain, and in vitro compositions comprising a determined amount of a natural human LDLR adaptin PTB domain and a ligand such as an NPXY (SEQ ID NO:7) peptide, or a determined amount of a natural human LDLR adaptin CC domain and ligand such as an LDL Receptor (SEQ ID NO:8) or a fragment thereof sufficient to selectively bind said domain.

The LDLR adaptin reagents are used, inter alia, in rational drug screening methods. An exemplary method comprises the steps of combining a disclosed LDLR adaptin reagent with a ligand and an agent under conditions wherein but for the presence of the agent, the domain and ligand engage in a first binding; and detecting a second binding of the domain and ligand, wherein a difference between the first and second bindings indicates the agent modulates the binding of the domain and the ligand. In other embodiments, the assay is a NMR-based assay wherein the detecting step comprises detecting a binding-dependent NMR shift in the mixture.

The invention also provides polynucleotides encoding the subject LDLR adaptin polypeptides, including natural coding sequences. Natural coding sequence polypeptides may be used as probes or primers for detecting or amplifying LDLR adaptin genes and transcripts. Accordingly, the invention also provides methods for detecting a mutation or polymorphism in a natural human LDLR adaptin gene in a patient predetermined to have or be predisposed to hypercholesterolemia, comprising the steps of detecting a natural, endogenous human LDLR adaptin gene or protein in the patient; and determining if the gene or protein structure or expression is associated with hypercholesterolemia or a predisposition to hypercholesterolemia. In this method, the detecting step may comprise, for example, detecting a natural, endogenous LDLR adaptin gene by specific probe hybridization, or detecting a natural, endogenous LDLR adaptin protein by specific antibody binding.

In a particular embodiment, the method is extended to therapeutic intervention by further comprising the steps of modulating the gene or protein structure or expression, and confirming a resultant change in cholesterol level of the patient, particularly wherein the modulating step comprises enhancing or stabilizing binding of the protein to an NPXY peptide. A wide variety of methods are disclosed for modulating the LDLR adaptin protein, including protein modulated with antisense polynucleotides, intrabodies, a dominant negative LDLR adaptin mutant, or a product of a disclosed rational drug screen.

BRIEF DESCRIPTION OF THE FIGURES

FIG. 2B. LDLR adaptin amino acid sequences of SEQ ID NOS: 2, 4 and 6.

DESCRIPTION OF PARTICULAR EMBODIMENTS OF THE INVENTION

Figure 1A:
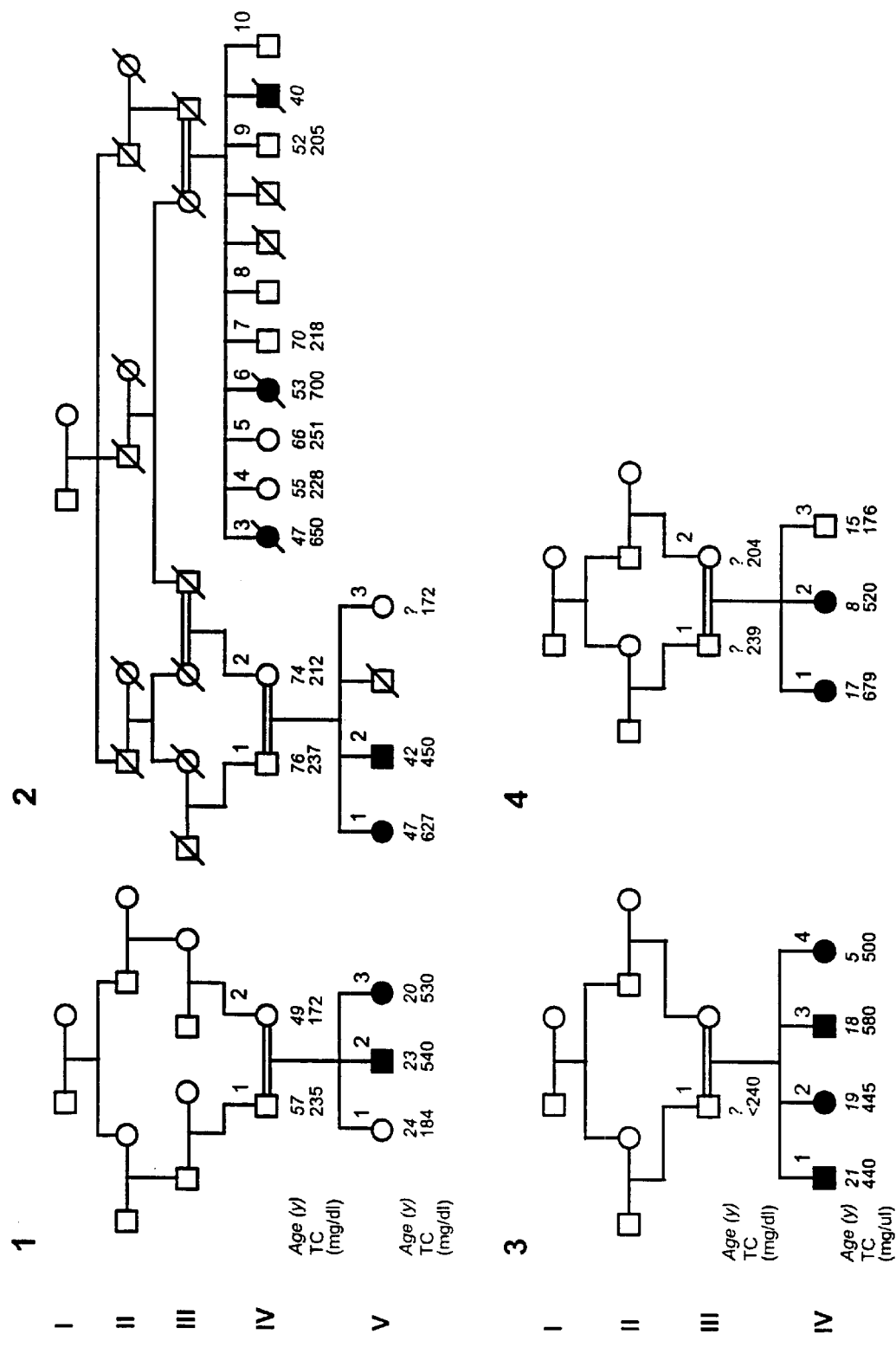
FIG. 1A. ARH pedigrees.

The nucleotide sequences of cDNAs of natural alleles encoding LDLR adaptin polypeptides from human, mouse and Xenopus are shown as SEQ ID NOS:1, 3 and 5, respectively, and the full translates are shown as SEQ ID NOS:2, 4 and 6, respectively. As described in further detail below, these translates include conserved PTB and conserved C-terminal (CC) domains. Those skilled in the art possess a wide variety of molecular and biochemical methods for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

In one embodiment, the invention provides a recombined natural human LDLR adaptin PTB domain. Natural means that the domain has the sequence of a natural human LDLR adaptin PTB domain as naturally present in a human subject. Recombined means that the domain is immediately flanked on at least one side by other than its natural immediate flanking residues in the native protein. For example, a subject PTB domain may consist only of the LDLR adaptin PTB domain, or it may consist of such domain joined immediately on its N and/or C-terminus to one or more additional moieties and/or functionalities, such as labels, heterologous amino acid residues, i.e. other than the native adaptin flanking residues, etc. Preferred LDLR adaptin PTB domains selectively bind the NPXY (SEQ ID NO:7) PTB-binding consensus motif, and preferably show more selective binding for the NPVY (residues 825–828 of SEQ ID NO:8), and even more so the NPVYQ (residues 825–829 of SEQ ID NO:8) motif of LDLR, though natural mutant LDLR adaptins may have PTB domains that have altered or disrupted NPXY binding function. Given the disclosed sequence information and methodologies, those skilled in the art can readily define and determine the sequences of the LDLR adaptin gene and protein of any given human subject.

The PTB domain of SEQ ID NO:2 is bound by residues 48–175; PTB domains of alternative LDLR adaptin molecules, particularly natural mutants, polymorphisms and alternate species are readily defined by alignments. For example, the alignment of FIG. 2B shows the corresponding PTB domain of mouse and Xenopus are also bound by residues 48–175 of natural LDLR adaptins of those species. Exemplary PTB domains of natural human LDLR adaptin mutants and polymorphisms are shown in Table 1 and described further below.

TABLE 1

Exemplary human LDLR Adaptin PTB domain polymorphisms and mutations.

| Ref. | Nucleotide change vs. SEQ ID NO:1, nucl. 142–525 | Amino acid change vs. SEQ ID NO:2, residues 48–175 |
| --- | --- | --- |
| ARH1 | insA432 | FS170Stop |
| ARH3 | C > T406 | Q136Stop |
| PRH5 | C > G239 | A > G80 |
| PRH12 | insAA519 | FS; V > K174, S > C175 |
| PRH26 | C > A480 | silent |

Similarly, the CC domain of SEQ ID NO:2 is bound by residues 248–276 of SEQ ID NO:2. CC domains of alternative LDLR adaptin molecules, particularly natural mutants, polymorphisms and alternate species are readily defined by alignments. For example, the alignment of FIG. 2B shows the corresponding CC domain of mouse and Xenopus are also bound by residues 248–276 of natural LDLR adaptins of those species. Exemplary CC domains of natural human LDLR adaptin mutants and polyporphisms are also shown in Table 2 below.

TABLE 2

Exemplary human LDLR Adaptin CC domain polymorphisms and mutations.

| Ref. | Nucleotide change vs. SEQ ID NO:1, nucl. 742–828 | Amino acid change vs. SEQ ID NO:2, residues 248–276 |
| --- | --- | --- |
| PRH38 | T > A778 | S > M260 |
| PRH91 | delGG760 | FS:257Stop |
| PRH44 | G > C753 | silent |
| PRH15 | C > G814 | L > V272 |
| PRH73 | T > C743 | V > A248 |

In another embodiment, the invention provides compositions comprising determined amounts of a natural human LDLR adaptin PTB or CC domain and a ligand thereof. Such compositions find particular use in cell based and in vitro assays for PTB function. Note that the adaptin domain component of these compositions need not be recombined and hence may comprise natural human LDLR adaptin proteins. In a particular embodiment, the domain is a PTB domain and the ligand comprises, and preferably consists essentially of, an NPXY peptide, particularly a NPVY peptide. In another embodiment, the ligand comprises, and preferably consists essentially of, an LDLR (SEQ ID NO:8), or a fragment thereof sufficient to selectively bind the PTB or CC adaptin domain as may be determined by binding and interaction assays disclosed herein.

The invention provides efficient methods of identifying agents, compounds or lead compounds for agents active at the level of an LDLR adaptin modulatable cellular function. Generally, these screening methods involve assaying for compounds which modulate the interaction of a subject LDLR adaptin polypeptide with a ligand and/or natural binding target. A wide variety of assays for binding agents is provided including labeled in vitro protein-ligand binding assays, cell based assays, immuoassays, etc. A wide variety of formats may be used, including co-immunoprecipitation, 2-hybrid transactivation, fluorescent polarization, NMR, fluorescent resonance energy transfer (FRET), transcriptional activation, etc. For example, a wide variety of NMR-based methods are available to rapidly screen libraries of small compounds for binding to protein targets (Hajduk, P. J., et al. Quarterly Reviews of Biophysics, 1999. 32 (3): 211–40). The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro ligand binding assays employ a mixture of components including an LDLR adaptin polypeptide, which in particular embodiments is part of a fusion product with another peptide or polypeptide, e.g. a tag for detection or anchoring, etc. The assay mixtures comprise a ligand, which term is used generically to encompass specific binding targets, preferably targets which naturally bind LDLR adaptin, such as an LDLR or fragment thereof. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc.

One type of library we use is a "directed" library, consisting of 100–200 compounds whose structures are based on common structural elements of PTB domain binding peptide ligands. Chemical databases are searched with these criteria, starting with substructures that match common frameworks of PTB domain ligands. Additional geometric criteria are obtained from observations that protein-binding ligands are inherently biased towards certain chemical architectures (Fejzo, J., et al. Chemistry and Biology, 1999. 6:755–769; Hajduk, P. J., et al. J. American Chemical Society, 2000. 122:7898–7904). Many of these architectures are aromatic-rich and include the general structures. We also screen larger libraries (1000–2000 compounds) that are designed to cover a wider range of chemical structures while still taking advantage of the observed biases of protein-binding ligands. Compounds in this library are also chosen with an emphasis towards later use in synthetic approaches, with relatively low formula weight (100–200Da) and composition of functional groups. In addition, we have adapted several PTB domain protein binding assays to high throughput screening (HTS). A compound collection initially consisting of roughly 350,000 drug-like chemicals has been collected, organized and extensively characterized in over 100 independent HTS assays. Such efforts have enabled the discovery of a large number of chemicals that potently and selectively modulate the activities of a broad range of polypeptide targets. The compound library has produced numerous drug entities that, following extensive optimization by medicinal chemistry, are in various phases of clinical and pre-clinical testing.

The resultant mixture is incubated under conditions whereby, but for the presence of the candidate pharmacological agent, the LDLR adaptin polypeptide specifically binds the ligand with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the LDLR adaptin polypeptide and one or more ligands is detected by any convenient way. For example, one of the LDLR adaptin polypeptide and ligand may be immobilized, and the other labeled; then in a solid-phase format, any of a variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the LDLR adaptin polypeptide to the ligand in the absence of the agent as compared with the binding affinity in the presence of the agent indicates that the agent modulates the binding of the polypeptide to the ligand. A difference, as used herein, is statistically significant and preferably represents at least a 50%, more preferably at least a 90% difference.

Accordingly, the subject LDLR adaptin domains and compositions find particular use in commercial drug screens. In one embodiment, the invention provides methods of using a subject recombined natural human LDLR adaptin PTB domain, comprising the steps of: combining the domain with an NPXY peptide and an agent under conditions wherein but for the presence of the agent, the domain and peptide engage in a first binding; and detecting a second binding of the domain and peptide, wherein a difference between the first and second bindings indicates the agent modulates the binding of the domain and the peptide. In another embodiment, the invention provides a method of using compositions comprising determined amounts of a natural human LDLR adaptin PTB or CC domain and a ligand thereof, comprising the steps of: contacting the composition with an agent under conditions wherein but for the presence of the agent, the domain and ligand engage in a first binding; and detecting a second binding of the domain and ligand, wherein a difference between the first and second bindings indicates the agent modulates the binding of the domain and the ligand. In preferred screens the second binding is greater than the first, indicating the agent enhances or stabilizes binding of the domain and the ligand. The preferred ligand for the PTB domain consist essentially of an NPXY peptide, or more preferably, a corresponding LDLR peptide such as the NPVY and NPVYQ peptide ligands disclosed herein.

The invention also provides polynucleotides encoding the subject LDLR adaptin polypeptides. The amino acid sequences of the subject polypeptides are used to back-translate polypeptide-encoding polynucleotides optimized for selected expression systems (Holler et al. (1993) Gene 136, 323–328; Martin et al. (1995) Gene 154, 150–166) or used to generate degenerate oligonucleotide primers and probes for use in the isolation of natural LDLR adaptin polypeptide-encoding polynucleotide sequences ("GCG" software, Genetics Computer Group, Inc, Madison Wis.). LDLR adaptin polypeptide-encoding nucleic acids are used in expression vectors and incorporated into recombinant host cells, e.g. for expression and screening, transgenic animals, e.g. for functional studies such as the efficacy of candidate drugs for disease associated with LDLR adaptin-modulated cell function, etc. In a particular embodiment, these polynucleotides comprise a natural LDLR domain coding sequence, including natural polymorphisms and mutations. For example, in the natural LDLR adaptin allele shown as SEQ ID NO:1, the PTB domain is nucleotides 142–525 and CC domain is 742–828.

The invention also provides polynucleotides comprising a doubly recombined sequence within a natural coding sequence of a natural human LDLR adaptin PTB or CC domain, wherein the polynucleotide provides a probe that specifically hybridizes with the corresponding PTB or CC domain. Doubly recombined means that the sequence is immediately flanked on both sides by other than its natural immediate flanking residues in the natural coding sequence. In a related embodiment, the invention also provides polynucleotides consisting of a sequence within a natural coding sequence of a natural human LDLR adaptin PTB or CC domain, wherein the polynucleotide provides a probe that specifically hybridizes with the corresponding PTB or CC domain.

These natural sequence LDLR adaptin polynucleotides provide hybridization probes and replication/amplification primers having a disclosed LDLR adaptin domain encoding cDNA sequence or fragments thereof sufficient to effect specific hybridization thereto. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7,0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C with 0.2×SSPE buffer at 42° C.

TABLE 3

Exemplary LDLR adaptin PTB domain encoding polynucleotides which hybridize with a strand of SEQ ID NO:1 under Conditions I and/or II.

| LDLR adaptin Nucleic Acids | Hybridization |
| --- | --- |
| SEQ ID NO:1, nucleotides 142–164 | + |
| SEQ ID NO:1, nucleotides 185–218 | + |
| SEQ ID NO:1, nucleotides 249–272 | + |
| SEQ ID NO:1, nucleotides 263–286 | + |
| SEQ ID NO:1, nucleotides 297–320 | + |
| SEQ ID NO:1, nucleotides 321–344 | + |
| SEQ ID NO:1, nucleotides 345–368 | + |
| SEQ ID NO:1, nucleotides 369–392 | + |
| SEQ ID NO:1, nucleotides 393–416 | + |
| SEQ ID NO:1, nucleotides 417–440 | + |
| SEQ ID NO:1, nucleotides 442–465 | + |
| SEQ ID NO:1, nucleotides 491–511 | + |
| SEQ ID NO:1, nucleotides 511–525 | + |

TABLE 4

Exemplary LDLR adaptin CC domain encoding polynucleotides which hybridize with a strand of SEQ ID NO:1 under Conditions I and/or II.

| LDLR adaptin Nucleic Acids | Hybridization |
| --- | --- |
| SEQ ID NO:1, nucleotides 742–770 | + |
| SEQ ID NO:1, nucleotides 775–789 | + |
| SEQ ID NO:1, nucleotides 784–809 | + |
| SEQ ID NO:1, nucleotides 799–824 | + |
| SEQ ID NO:1, nucleotides 801–828 | + |

A wide variety of alternative polynucleotide embodiments may be practiced, including isolated, i.e. unaccompanied by at least some of the material with which it is associated in its natural state, preferably constituting at least about 0.5%, preferably at least about 5% by weight of total nucleic acid present in a given fraction. In addition, it is often advantageous to use polynucleotides comprising other than DNA or RNA bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of LDLR adaptin domain genes and gene transcripts and in detecting or amplifying nucleic acids encoding additional LDLR adaptin domain homologs and structural analogs. In diagnosis, LDLR adaptin hybridization probes find use in identifying polymorphic and mutant LDLR adaptin alleles in clinical and laboratory samples. Mutant alleles are used to generate allele-specific oligonucleotide (ASO) probes for high-throughput clinical diagnoses. In therapy, therapeutic LDLR polynucleotides are used to modulate cellular expression or intracellular concentration or availability of active LDLR adaptin.

Accordingly, in one embodiment, the invention provides methods for detecting a mutation or polymorphism in a natural human LDLR adaptin gene in a patient predetermined to have or be predisposed to hypercholesterolemia, comprising the steps of detecting a natural, endogenous human LDLR adaptin gene or protein in the patient; and determining if the gene or protein structure or expression is associated with hypercholesterolemia or a predisposition to hypercholesterolemia. For example, the detecting step may comprise detecting a natural, endogenous LDLR adaptin gene allele by specific probe hybridization. Alternatively, the allele may be detected inferentially, by detecting the encoded LDLR adaptin polypeptide. In another embodiment, the detecting step comprises detecting a natural, endogenous LDLR adaptin protein by specific antibody binding.

These diagnostic aspects of the invention may be combined to effect therapy. For example, the method may further comprise the steps of modulating the gene or protein structure or expression, and confirming a resultant change in cholesterol level of the patient. In more particular embodiments, the modulating step comprises enhancing or stabilizing binding of the protein to a ligand, such as an NPXY peptide. In other more particular embodiments, the gene or protein structure or expression is modulated with antisense polynucleotides, intrabodies, a dominant negative LDLR adaptin mutant, or an agent identified in the disclosed drug screens.

The following experimental section and examples are offered by way of illustration and not by way of limitation.

EXAMPLES

I. Mutations in an LDL Receptor Adaptor Protein Cause Autosomal Recessive Hypercholesterolemia The liver is the major site of synthesis and clearance of cholesterol ester-rich lipoproteins. Over 70% of circulating LDL is removed from the blood via hepatic LDLR-mediated endocytosis (1). In individuals with two mutant LDLR alleles (homozygous FH), the rate of clearance of LDL from the blood is markedly decreased, resulting in hypercholesterolemia, xanthomatosis and premature coronary artery disease (CAD) (1). LDLR activity in cultured skin fibroblasts from FH homozygotes is also markedly reduced (1). FH heterozygotes have a 50% reduction in LDL receptors and moderate hypercholesterolemia. In 1973 Khachadurian described an unusual Lebanese family in which four siblings had the clinical features of homozygous FH, including severe hypercholesterolemia (mean plasma cholesterol level of 728 mg/dl), huge tendon xanthomas, and premature CAD (2), but only a modest reduction in LDLR activity in cultured fibroblasts (3). The parents of the four siblings were normocholesterolemic (2). Subsequently, additional subjects with an autosomal recessive form of hypercholesterolemia and normal fibroblast LDLR function were described (4–9), including five families from Sardinia (7–9). As compared to normal subjects, two of the Sardinian probands had a four-fold reduction in the rate of clearance of plasma LDL, which was similar to the reduction observed in an FH homozygote studied simultaneously (8).

To elucidate the molecular basis of ARH, we performed a whole genome linkage study in four ARH families (FIG. 1A; Table 5), including the families of the two Sardinian patients with low LDL clearance rates (ARH1 and ARH2) (8), the index family described by Kachadurian (ARH3) (2), and a second Lebanese family (ARH4).

For the data of Table 5, genomic DNA was extracted from cultured fibroblasts or leukoctyes. The coding regions of the gene were screened for sequence variation using SSCP and dideoxy-sequencing. No mutations were found in 50 unrelated Sardinians or 22 unrelated Lebanese subjects. The nucleotides and amino acids were numbered from the A of the initiation codon (ATG). The age at the time of diagnosis is provided. The plasma cholesterol and LDL-cholesterol levels (when available) were measured by the referring physician. LDLR activity was assessed as described in the reference and is provided as a percentage of normal control fibroblasts studied simultaneously. Abbreviations: C, fasting plasma cholesterol (mg/dl); ref., reference; F, female; M, male; ins, insertion, FS, frameshift producing a premature termination amino acid indicated; tuberous or plantar describe the type of xanthomas; +, indicates presence of xanthelasmas, Cath, coronary artery catheterization; y, years; CABG, coronary artery bypass surgery; NIDDM, noninsulin dependent diabetes; ETT, exercise tolerance test; MI, myocardial infarction; amino acids: W, tryptophan; Q, glutamine; P, proline; H, histidine.

Figure 1B:
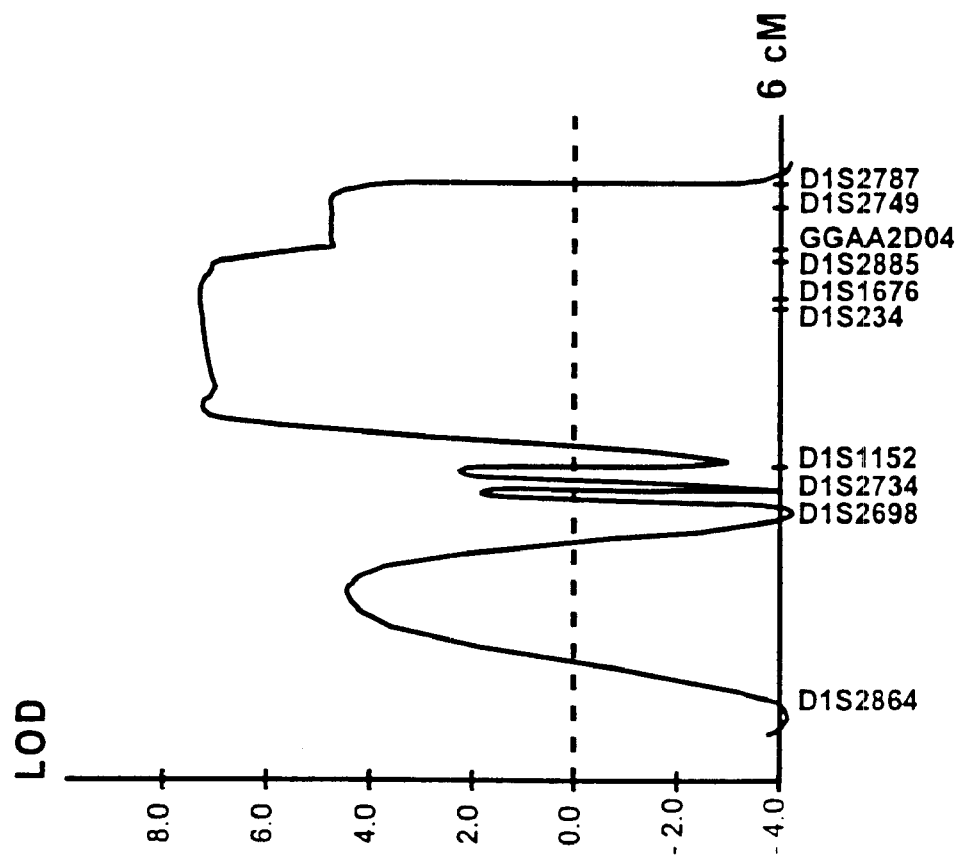
FIG. 1B. ARH linkage analysis.
Figure 1C:
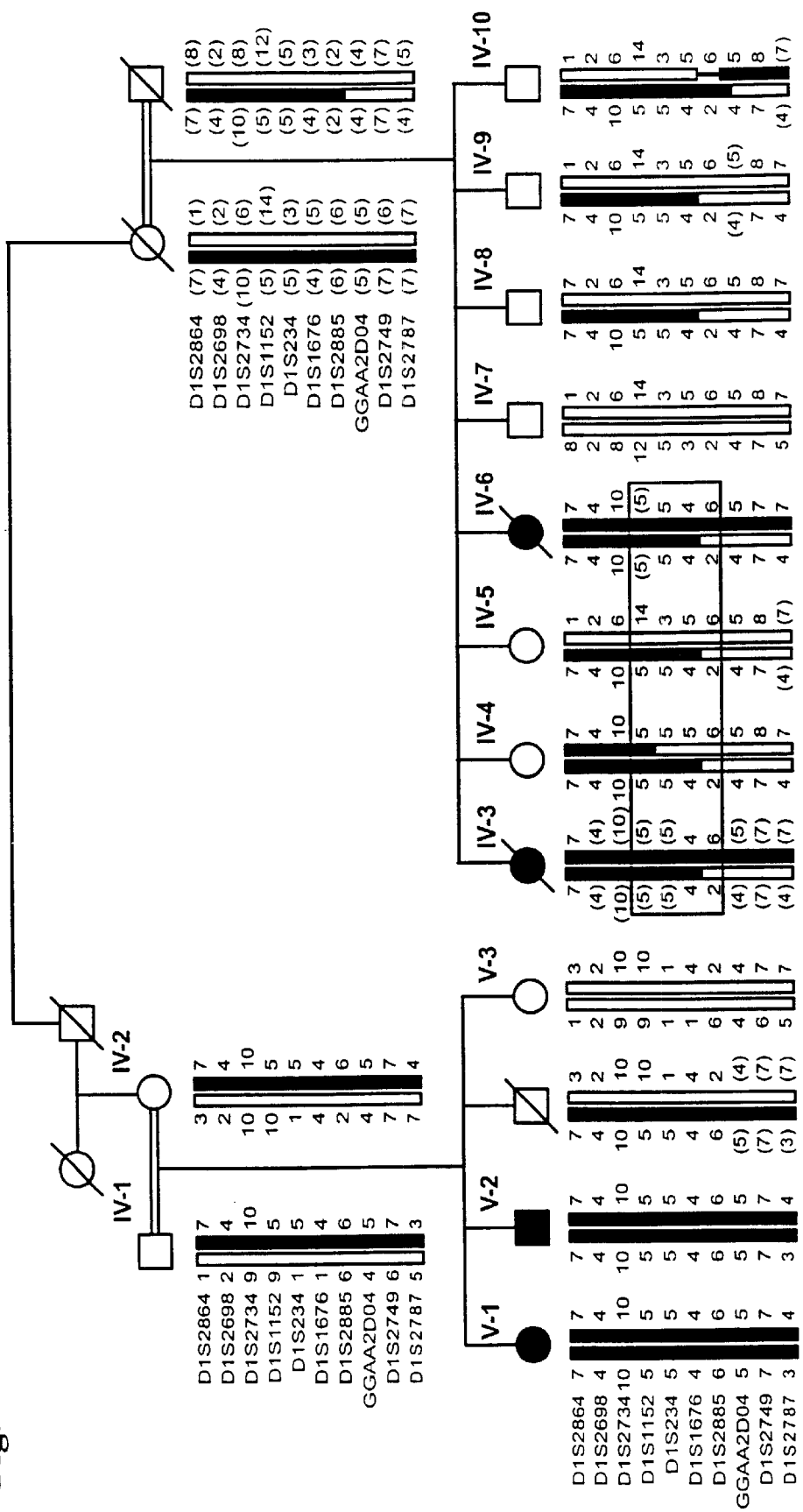
FIG. 1C. ARH genetic fine mapping.

FIG. 1A shows the four pedigrees employed for gene mapping (ARH 1– ARH4). ARH1 and ARH2 are Sardinians and ARH3 and ARH4 are Lebanese. Fasting plasma total cholesterol levels (when available) are shown. The demographics and clinical characteristics of the probands in these families are provided in Table 5. FIG. 1B shows the distribution of LOD scores in the linked region on chromosome 1. A total genome scan was performed initially in ARH1 and ARH2 and then additional markers were typed in all four families. The maximum LOD score was 7.4 over a ~6 cM region on chromosome 1. FIG. 1C shows fine mapping within the linked region in ARH2. Genomic DNA was extracted from whole blood that had been collected from the deceased probands and stored at −20° C. for over ten years, or from fresh leukocytes isolated from venous blood. The region of homozygosity shared by the affected individuals in this family is boxed. Squares, males; circles, females; double lines, consanguineous matings; filled squares, affected individuals.

The probands of the four families were offspring of consangunious unions and all families showed horizontal transmission of the hypercholesterolemia, which is consistent with autosomal recessive inheritance of a rare gene defect. Affected family members were severely hypercholesterolemic (plasma LDL-cholesterol levels ranging from 400–600 mg/dl) and had normal triglyceride and HDL-cholesterol levels (data not shown). All had xanthomas and many had xanthelasmas, aortic. stenosis and premature CAD (Table 5). The plasma LDL levels tend to be lower and the onset of symptomatic-CAD is somewhat later in ARH than in FH homozygotes. The xanthomas tend to be extremely large. For example, one affected family member in ARH2 required specially tailored trousers to accommodate large, tuberous xanthomas on his knees. LDLR function studies in cultured fibroblasts from representative affected family members were normal or only moderately reduced (3,7,8), thus ruling out a diagnosis of homozygous FH.

Multipoint linkage analysis revealed significant linkage (LOD score 7.4) to a 5.7 cM interval on 1p35, demarcated by the polymorphic loci D1S2864 and D1S2787 (FIG. 1B) (10). This interval is adjacent to a chromosomal region on 1p35–p36 linked to ARH in two other families (11). We found no linkage to 15q25–q26, which was previously found to be associated with ARH in five Sardinian families (9), including ARH1 (FIGS. 1A–1C). The linked region was refined to an ~1 cM interval extending from D1S1152 to D1S2885 by identifying a region of homozygosity shared by all affected family members in ARH2 (FIG. 1C) (12). The coding sequences of 32 genes that mapped to this interval were screened for sequence variation using PCR and single strand conformation polymorphism (SSCP) technique (13). Two abnormally-migrating bands were identified in the predicted coding sequences of a cDNA (DKFZp586D0624) in probands from ARH1 and ARH3.

The cDNA for DKFZp586D0624 was amplified by PCR of reverse transcribed liver poly(A)$^+$ mRNA. A $P_1$ clone containing the entire gene (290N7, Incyte, Inc.) was used to amplify the introns and to sequence intron-exon boundaries. The gene structure and predicted amino acid sequence of the encoded protein are shown in FIG. 2.

Figure 2A:
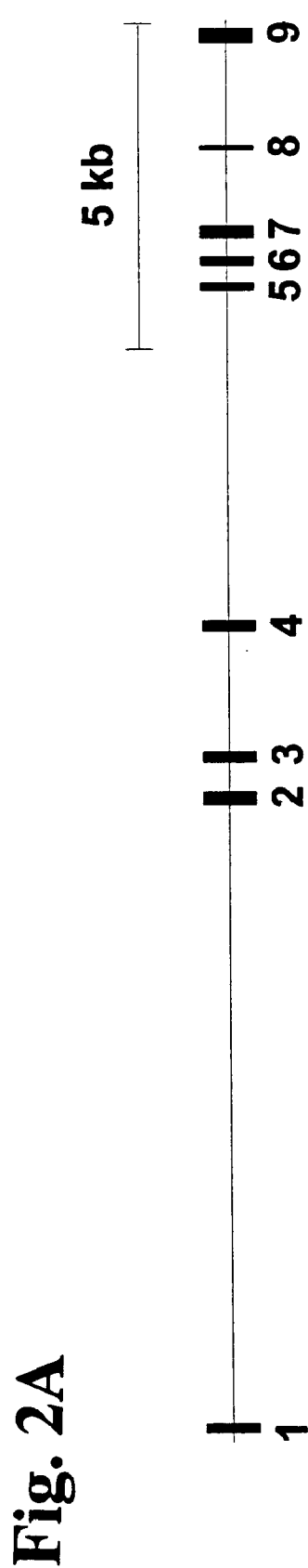
FIG. 2A. LDLR adaptin gene structure.
Figure 2C:
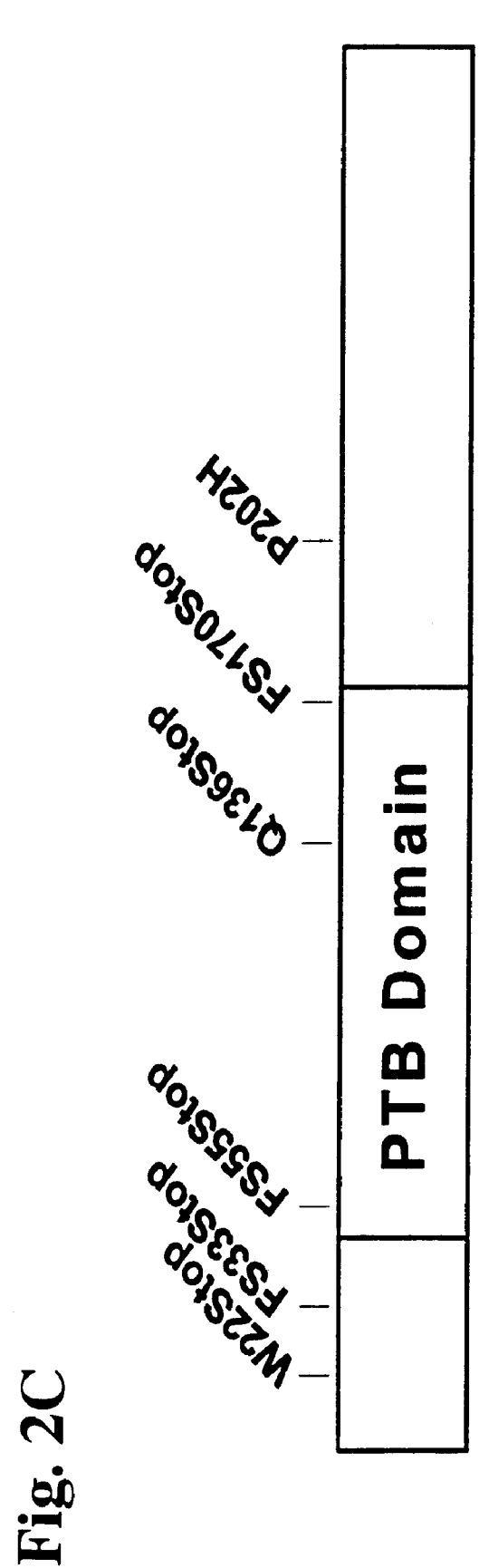
FIG. 2C. Location of LDR adaptin mutations in ARH probands.

FIG. 2A shows the LDLR adaptin is encoded by nine exons and spans ~25 kb. Filled rectangles, exons; lines, introns. FIG. 2B shows the predicted amino acid sequences of human, mouse and Xenopus LDLR adaptin. Numbers to the right correspond to human sequence. The alignment of the inferred amino acid sequences displays 67% identity among the three proteins. The regions of amino acid identity are boxed. LDLR adaptin has a highly conserved PTB domain at the amino terminus (89% identity), which is aligned to the closest paralog with determined spatial structure, the PTB domain of Drosophila melanogaster NUMB (PDB entry 2NMB, chain A, residues 14–154) (35). Alignment is constructed with PSI-BLAST (23). The boundaries of the PTB domain are according to Pfam 6.0 database (36,37; domain PF00640). FIG. 2C is a schematic representation of LDLR adaptin showing the location of the mutations identified in this study.

The gene spans ~20 kb and has nine exons and eight introns (FIG. 2A). The predicted amino acid sequence contains a 170-amino acid motif that shares significant sequence similarity to the phosphotyrosine binding (PTB) domains of several adaptor proteins (FIG. 2B) (14,15). PTB domains bind the consensus sequence NPXY, which is present in the cytoplasmic domains of several cell surface receptors, including the epidermal growth factor receptor (16), the insulin receptor (17), nerve growth factor receptor (TrkA) (18), and the LDLR (Howell et al. 1999, Mol Cell Biol 19, 5179–5188). The integrity of the NPXY sequence in the cytoplasmic tail of the LDLR is absolutely required for internalization (19,20), and the LDLR has been shown in vitro to bind other proteins containing PTB domains (21,22). Proteins that bind to cytoplasmic tails of endocytic receptors are often called adaptins, and therefore we named the gene product LDLR adaptin.

Database searches (23) revealed orthologous proteins in mouse and Xenopus that share 89% sequence identity with the human protein in the PTB domain (FIG. 2B). In these orthologs, several regions in the C-terminal half of the protein are also highly conserved. These blocks do not appear to be shared with other proteins currently in the database. The closest paralogs of LDLR adaptin are the Drosophila protein NUMB (24) and the worm adaptor protein involved in cell engulfment, CED-6 (25), which share 33% (52%) and 34% (60%) sequence similarity with the human protein, respectively.

The coding region of LDLR adaptin was sequenced using genomic DNA from the affected family members of ARH1–ARH4 (FIG. 1). The affected individuals in ARHI1 were homozygous for a single basepair insertion in exon 4 (Table 5). The mutation disrupts the reading frame and introduces a premature termination codon at amino acid 170, truncating the protein in the terminal portion of the PTB domain. Affected individuals in ARH2 were homozygous for a G to A transition that produced a nonsense mutation at codon 22. The LDLR adaptin gene was sequenced in 10 other unrelated Sardinian probands and mutations were found in both alleles of all subjects. Four of the Sardinian patients were homozygous for the frameshift mutation in exon 4 and three were homozygous for the nonsense mutation in exon 1. The remaining three probands were compound heterozygotes for the two mutations. The finding that only two mutations account for ARH in these 12 apparently unrelated Sardinian probands is consistent with a founder effect, which has been observed for other diseases on the island (26,27). In general, the frameshift mutation was more common in the northern region of Sardinia, and the nonsense mutation more frequent in the central and southern part of Sardinia, although there was significant overlap in the distribution. Neither mutation was found in 50 normoplipidemic Sardinians.

The four affected Lebanese siblings in ARH3 (FIGS. 1A–1C) were homozygous for a nonsense mutation in codon 136, which stops translation in the terminal region of the PTB binding domain. Cultured fibroblasts from two of these siblings had an ~50% reduction in LDLR activity (3). Both probands in ARH4 were homozygous for a missense mutation that substitutes a histidine for proline at amino acid 202, which is not located in the PTB domain. Cultured fibroblasts from the hypercholesterolemic siblings in this family had completely normal LDLR activity (3). Neither of the mutations found in ARH3 or ARH4 were present in 15 normolipidemic individuals from Lebanon or in seven unrelated Lebanese FH homozygotes with a molecularly-defined defect in the LDLR gene (28).

Two additional mutations were identified in families with normocholesterolemic parents and a single hypercholesterolemic offspring. Both mutations were frameshift mutations that are predicted to truncate the protein near the $NH_2$ terminus (FIG. 2C). A one basepair insertion (c.insG72;FS33Stop) was identified in an Iranian child with an LDL-cholesterol of 598 mg/dl whose normolipidemic parents were first-cousins. The second proband was an American child of a suspected incestuous relationship who had a single base deletion (c.delG71; FS55Stop). Both types that would suggest defective signaling or functioning of other NPXY-containing proteins, with the exception of probands who developed noninsulin dependent diabetes (Table 5).

TABLE 5

Molecular defects in LDLR adaptin and clinical characteristics of probands in four families with ARH (FIG. 1).

| Family | Nucleotide change | Amino acid change | Origin | Age/sex | Plasma C/LDL-C | LDLR activity in fibroblasts | Xanthomas/xanthelasma | Coronary artery disease | Comments | Ref |
|---|---|---|---|---|---|---|---|---|---|---|
| ARH1 | c.insA432 | FS170 | Bitti, Sardinia | 20/F | 530/460 | ~70% | Tuberous/+ | Asymptomatic Moderate (cath) | Aortic stenosis; 8 maternal relatives died < age 33 | 3, 7–9 |
|  |  |  |  | 23/M | 540/464 | ~80% | Tuberous/+ | Angina, 20 y Severe (cath) | Aortic stenosis |  |
| ARH2 | c.G > A65 | W22Stop | Villa Noras, Sardinia | 40/M | 650/ | Not done | Tuberous/+ | Angina |  | 8 |
|  |  |  |  | 53/F | 700/ | Not done | Tuberous/+ | Sudden death | NIDDM, age 49 |  |
|  |  |  |  | 47/F | 650/ | Not done | Tuberous/+ | CABG (42 y and 47 y) | C 369 on lipid-lowering Rx |  |
|  |  |  |  | 47/F | 627/550 | 80% | Tuberous/+ | Angina 42 y Severe (cath) |  |  |
|  |  |  |  | 42/M | 450/372 | 85% | Tuberous/+ | ETT normal |  |  |
| ARH3 | c.C > T406 | Q136Stop | Beruit, Lebanon | 21/M | 440 | 60%–70% | Tuberous | Asymptomatic | Father NIDDM | 2, 3 |
|  |  |  |  | 19/F | 445 |  | Tuberous | Asymptomatic |  |  |
|  |  |  |  | 18/F | 580 | 60%–70% | Tuberous | Asymptomatic |  |  |
|  |  |  |  | 5/F | 500 |  | Tuberous | Asymptomatic |  |  |
| ARH4 | cC > A607 | P202H | Lebanon | 17/F | 610/520 | 100% | Planar, at birth | Asymptomatic ETTnl, 14 y | Father, MI, 28 y | 3 |
|  |  |  |  | 7/F | 520/392 | 100% | Planar | Asymptomatic |  |  | mutations are located in the midst of a string of seven guanine residues in exon 1.

Northern blot analysis to assess the size and relative amount of the LDLR adaptin mRNA was performed in cultured fibroblasts from probands of ARH1, ARH3, and ARH4. A 3.1 kb mRNA was detected in the control fibroblasts. In contrast to the LDLR mRNA, the levels of LDLR adaptin mRNA were not affected by the presence of sterols in the medium. No LDLR adaptin mRNA was detected in the cells of the proband from ARH1 who had a nonsense mutation in the first exon. Only a trace amount of LDLR adaptin mRNA was present in the proband from ARH3, who was homozygous for a frameshift mutation that introduces a stop codon in exon 4. The marked reduction in mRNA levels in these two cell lines indicates nonsense mediated decay (29). A normal amount of mRNA was present in the proband from ARH4, who was homozygous for a missense mutation (ARH4). ARH4 was the only family in which the parents had evidence of a defect in cholesterol metabolism; the father reportedly had a myocardial infarction at age 28. In one ARH family described by Norman et al. (6), both parents had moderately elevated plasma LDL-cholesterol levels. These observations indicate that some LDLR adaptin mutations can result in co-dominant, rather than recessive hypercholesterolemia.

PTB domains differ in their selectivity for different NPXY sequences, which allows for specificity in the biological response (30). Other adaptor proteins, such as Drosophila SHC, bind to only a subset of NPXY sequences (30). ARH appears to be a close phenocopy of homozygous FH, which suggests that all clinical sequelae of LDLR adaptin mutations are attributable to defective LDLR activity. LDLR adaptin appears to be nearly ubiquitously expressed, as is the LDLR (1). However, LDLR expression is relatively low in some of the same tissues that express high levels of LDLR adaptin (kidney, placenta) (1). None of the 16 probands examined in this study have other obvious shared pheno- Numerical references for Example I.

1. J. L. Goldstein, H. H. Hobbs, M. S. Brown, in *The Metabolic and Molecular Bases of Inherited Disease,* C. R. Scriver, A. L. Beaudet, M.D, W. S. Sly, D. Valle, B. Childs, K. W. Kinzler, B. Vogelstein, Eds. (McGraw Hill, New York, ed. 8, 200 1), vol. II, chap. 120, p. 2863–2913.
2. A. K. Khachadurian, S. M. Uthman, *Nutr. Metab.* 15, 132–40 (1973).
3. J. L. Goldstein and M. S. Brown, unpublished observations.
4. M. Harada-Shiba, et al., *Arterioscler. Thromb.* 12, 1071–8 (1992).
5. H. H. Schmidt, et al., *Am. J. Cardiol.* 77, 575–80 (1996).
6. D. Norman, et al., *J. Clin. Invest.* 104, 619–28 (1999).
7. G. Zuliani, et al., *Eur. J. Clin. Invest.* 25, 322–31 (1995).
8. G. Zuliani, et al., *Arterioscler. Thromb. Vasc. Biol.* 19, 802–9 (1999).
9. M. Ciccarese, et al., *Am. J. Hum. Genet.* 66, 453–60 (2000).
10. A whole genome linkage analysis was performed. A total of 450 polymorphic DNA markers at ~8 cM intervals (Cooperative Human Linkage Center/Weber Human Screening Set Version 8, Research Genetics, Inc.) were genotyped from selected family members from ARH1 (IV.1, IV.2, V.1, V.2, V.3) and ARH2 (IV.1, IV.2, V.1, V.2, V.3) (FIG. 1). Linkage analysis using GENEHUNTER (33) and CRIMAP (34), ruled out linkage to 93% of the genome. An additional 70 genetic markers covering the 14 genomic regions that could not be excluded on the initial genome-wide screen were genotyped in all numbered members of the four families (FIG. 1A). Linkage to a region on 1p35 was found with a LOD score of 7.4. The affected siblings in ARH1 and ARH3 inherited alleles identical by descent in this region but were not homozygous for any of the markers. The two siblings of ARH4 shared a 44 cM region of homozygosity in this region.

11. E. Eden, R. Naoumova, J. Burden, M. McCarthy, A. Soutar, *Am. J. Hum. Genet.* 68, 653–660 (2001).
12. The centrometric boundary of homozygosity was defined by D1S2885 (family members IV.3 and IV.6 in ARH2), which is telomeric to GGAA2D04 on the physical map (ncbi.nlm.nih.gov). The telomeric boundary was delineated by marker D1S1152 in individual IV.4, who was normolipemic and yet was homozygous for the markers distal to D1S1152. The exact position of D1S1152 was determined through genetic analysis of crossovers in ARH2 and CEPH family no. 1362. The coding regions of the genes located in the physical region between markers D1S1152 and D1S2885 were screened for sequence variations.
13. M. Orita, Y. Suzuki, T. Sekiya, K. Hayashi, *Genomics* 5, 874–879 (1989).
14. M. M. Zhou, S. W. Fesik, *Prog. Biophys. Mol. Biol.* 64, 221–35 (1995).
15. P. Bork, B. Margolis, *Cell* 80, 693–4 (1995).
16. P. Blaikie, et al., *J. Biol. Chem.* 269, 32031–4 (1994).
17. W. He, T. J. O'Neill, T. A. Gustafson, *J. Biol. Chem.* 270, 23258–62 (1995).
18. A. Obermeier, et al., *EMBO J.* 13, 1585–90 (1994).
19. C. G. Davis, et al., *Cell* 45, 15–24 (1986).
20. W.-J. Chen, J. L. Goldstein, M. S. Brown, *J. Biol. Chem.* 265, 3116–3123 (1990).
21. M. Trommsdorff, J. P.-Borg, B. Margolis, J. Herz, *J. Biol. Chem.* 273, 33556–60 (1998).
22. M. Gotthardt, et al., *J. Biol. Chem.* 275, 25616–24 (2000).
23. S. F. Altschul et al., *Nucleic Acids Res.* 25, 3389–402 (1997)
24. J. A. Knoblich, L. Y. Jan, Y. N. Jan, *Proc Natl Acad Sci U S A* 94, 13005–10 (1997).
25. Q. A. Liu, M. O. Hengartner, *Cell* 93, 961–72 (1998).
26. M. C. Rosatelli, et al., *Am. J. Hum. Genet.* 50, 422–6 (1992).
27. G. Loudianos, et al., *Hum. Mutat.* 14, 294–303 (1999).
28. M. A. Lehrman, et al., *J. Biol. Chem.* 262, 401–410 (1987).
29. P. A. Frischmeyer, H. C. Dietz; *Hum. Mol. Genet.* 8, 1893–00 (1999).
30. S. Luschnig, J. Krauss, K. Bohmann, I. Desjeux, C. Nusslein-Volhard, *Mol Cell* 5, 231–41 (2000).
31. K. Matter, J. A. Whitney, E. M. Yamamoto, I. Mellman, *Cell* 74, 1053–64 (1993).
32. R. K. Pathak, et al., *J. Cell Biol.* 111, 347–59 (1990).
33. L. Kruglyak, M. J. Daly, M. P. Reeve-Daly, E. S. Lander, *Am J Hum Genet* 58, 1347–63 (1996).
34. E. S. Lander, D. Botstein, *Science* 236, 1567–70 (1987).
35. S. C. Li et al., *Nat. Struct. Biol.* 5, 1075–83 (1998).
36. A. Bateman, E. Bimey, E. Durbin, S. R. Eddy, K. L. Howe, E. L. Sonnhammer. *Nucleic Acids Res.* 28:263–6 (2000).
37. http://pfam.wustl.edu
38. E. V. Jokinen, et al., *J. Biol. Chem.* 269, 26411–26418 (1994).

II. Yeast Two-hybrid Screen for PTB Ligands.

To identify native tyrosine-phosphorylated ligands for the LDLR PTB domain, we use a modified yeast two-hybrid system with a yeast strain that also expressed a protein tyrosine kinase (Keegan, et al. 1996 Oncogene 12:1537–1544; Lioubin, et al. 1996 Genes Dev. 10:1084–1095), as adapted from Howell et al. 1999 Mol Cell Biol 19, 5179–5188. A detailed protocol for the modified yeast two-hybrid screen is provided elsewhere (Vojtek, et al. 1995 Methods Enzymol. 255:331–342). Briefly, the L40 strain of yeast, which has LexA operator sequences driving both HIS3 and lacZ reporter genes, is transformed with construct encoding a fusion protein containing an N-terminal LexA DNA binding domain followed by residues 1–175 of human LDLR adaptin. The strains are cotransformed with hepatocyte cDNAs expressed as fusion proteins with-the GAL4 activation domain from the pGAD-GH vector (Clontech). Transformants are plated on minimal medium lacking tryptophan and leucine to select for the LexA- and activation domain-encoding plasmids, respectively, and lacking histidine but containing 5 mM 3-amino-1,2,4-triazole to assay for transactivation of the HIS3 reporter. Colonies are picked after 3 days of growth. Yeasts are tested for β-galactosidase activity by filter lift assays (Howell, et al., EMBO J. 16:1165–1175), and colonies that produced stronger signals than the control yeast containing the LDLR adaptin PTB and pVP16 vectors alone after 2 h are identified for further analysis. Library isolates are retested for transactivation in yeast expressing either the LexA-lamin control fusion or the LexA-PTB domain fusion in the absence of the Fms kinase. Those isolates that expressed less β-galactosidase activity than the vector-alone controls with LexA-lamin are not analyzed further. The remainder are isolated as plasmid DNAs and sequenced by using a BioSequencer (Applied Biosystems) with the pGAD-GH5' oligonucleotide (Clontech) or the M13 Forward oligonucleotide (Stratagene). Database searches are done with Blast, which is available at the National Center for Biotechnology Information website.

III. Filter Binding Assay: Optimizing LDLR Adaptin PTB Domain Peptide Ligand Sequence We test the ability of the PTB domain to interact directly with synthetic peptides in a filter binding assay based on the sequences identified in the two-hybrid screen in a protocol adapted from Howell et al. 1999 Mol Cell Biol 19, 5179–5188. Arrays of peptides are synthesized on cellulose membranes as described previously (Frank, 1992, Tetrahedron 48:9217–9232; Frank, et al. 1996 Methods Mol. Biol. 66:149–169) with an ABIMED ASP 222 automated SPOT-robot. Filters are blocked with 10% fetal bovine serum in TBST (100 mM Tris Cl [pH 7.5], 150 mM NaCl, 1% Tween 20) for 1 h at 25° C., incubated with the $^{32}$P-label GSTag-Dabl PTB domain (0.1 μg/ml, 2.5×10$^6$ cpm/ml) for 18 h at 4° C., and then washed several times with TSBT prior to autoradiography or quantitation using a PhosphorImager (Molecular Dynamics). To prepare the $^{32}$P-labelled GSTag-PTB domain, 10 μg of the fusion protein immobilized on glutathione agarose is incubated with PKA (New England Biolabs) and γ-$^{32}$PATP at 10 μCi/μl for 30 min at 30° C. in the buffer provided by the manufacturer. Unincorporated radioactivity is removed, and the labelled fusion protein is eluted with 20 mM reduced glutathione in PBS.

Briefly, a GST-PTB domain fusion protein is purified and labelled by phosphorylation with PKA and radioactive ATP. The purified, radioactive fusion protein is then incubated with a sheet of cellulose paper on which different 15-residue peptides had been synthesized directly. Each sheet contains up to 100 different peptide sequences. After incubation, the sheets are washed and exposed to film and bound radioactivity is quantified. Peptides with phosphotyrosine in place of the tyrosine of the NPXY sequence (i.e., NPXpY peptides) are also tested. To determine which residues in the LDLR sequence might be involved in the interaction, we synthesize an array of peptides based on the LDLR sequence with an alanine substitution at each position in turn. The ability of each peptide to bind to the PTB domain is compared to that of the wild type. In order to determine what features of the side chains in the APP peptide were recognized by the PTB domain, each critical residue identified is replaced with all 19 amino acids except cysteine.

IV. Fluorescence Polarization

Peptide binding to the GST-PTB domain fusion protein is measured by using fluorescence polarization (also known as fluorescence anisotropy; Li, et al. 1997 Proc. Natl. Acad. Sci. USA 94:7204–7209) is a protocol adapted from Howell et al. 1999 Mol Cell Biol 19, 5179–5188. A 16-mer LDLR peptide (acetyl-SINFDNPVYQKTTEDE-amide, residues 820–835 of SEQ ID NO:8) and its phosphorylated analog (phosphate on the tyrosine) are synthesized with an AMS 222 Multiple Peptide Synthesizer using TenetaGel S resin (Rapp Polymere) and purified by high-pressure liquid chromatography. Peptide concentrations are determined by spectrophotometry and confirmed by amino acid analysis. Fifty nanomoles of peptide is reacted with 100 nmol of fluorescein-C6-succinimidyl ester (FXS; PanVera Corporation, Madison, Wis.) in 50 μl of 10% dimethyl sulfoxide-0.1 M potassium phosphate (pH 8.2) for 1 h at 37° C. Reactions are stopped with 5 μmol of Tris HCl (pH 8.0) and analyzed by thin-layer chromatography (Silica gel 60; methanol-acetic acid-water [4:1:1]). A fluorescent product at an Rf of 0.3 was eluted in 10 mM Tris HCl (pH 8.0)–1 mM EDTA. Based on fluorescence intensity, the fluorescent peptide (probe) concentration in binding reaction mixtures was estimated to be 20 nM.

Binding measurements are performed in a Beacon 2000 Variable Temperature Fluorescence Polarization System (PanVera Corporation). Essentially, a constant concentration of fluorescent probe peptide is incubated with various concentrations of the GST-PTB domain or GST in 100 μl of 0.5% Triton X-100-20 mM glutathione-200 mM Tris HCl (pH 8.0) at 4° C. and fluorescence polarization is measured. Steady-state probe-to-protein binding is calculated from the linear relationship between polarization and the proportion of the probe bound. Actual polarization values range from 92.4 units (free probe) to 254.1 mP (100-fold excess of GST-PTB domain). Binding reaches 95% of maximum after 5 min at 4° C. A Hill plot is linear with a slope of 1.0, indicating noncooperative binding. Competition experiments use a constant mixture of GST-PTB domain (1.1 μM), probe (20 nM), and buffer to which various concentrations of nonfluoresceinated synthetic peptide or its phosphorylated analog are added. To dephosphorylate the competitor phosphopeptide, we add potato acid phosphatase (0.05 U; Sigma, St. Louis, Mo.) to selected tubes and incubate them for 60 min at room temperature before cooling them to 4° C. and measuring the polarization. To determine the effect of added phospholipids on GST-PTB domain binding to the probe, we add the probe to a standard unilamellar vesicle (LUV)-GST-PTB domain binding reaction mixture (see below) before reading the fluorescence polarization.

V. NMR-based PTB Domain/ligand HTS

Library compounds are maintained as 1M stocks in deuterated DMSO, and LDLR adaptin PTB domain protein samples checked to ensure that DMSO does not bind with any significant affinity. Samples of $^{15}N/^{13}C$-methyl labeled protein (250 μM) are mixed with 3–10 compounds at 1 mM each, which is sufficient to find ligands with weak (millimolar) dissociation constants. Protein chemical shifts are recorded using $^{13}C/^{1}H$ HSQC as our primary method, complemented by $^{15}N/^{1}H$ HSQC. Spectra from ligand-containing solutions are compared to those from ligand-free samples, calculating chemical shift changes with the minimum chemical shift difference method (Farmer, B. T. I., et al. Nature Structural Biology, 1996. 3:995–997). Where significant changes are observed, we deconvolute the binding of each ligand in the mixture by examining new samples with single protein/ligand mixtures. Compounds that demonstrate binding are titrated into a sample of $^{15}N$-labeled protein to measure dissociation constants, which can be measured by NMR if the complex is in fast exchange ($K_d > 10$ μM).

Screening throughput of this method exceeds 1000 compounds per day for the initial screen: 15 minutes per sample and 10 ligands/sample. We use several sources of structure-activity relationship information available from the first round of screening to generate small secondary libraries which are subsequently screened for compounds with higher affinity. Comparisons of the affinity of structurally-related compounds identify positions on ligands that are essential for binding. Additionally, comparisons of the chemical shift changes caused by related ligands rapidly identify the relative orientation of protein/ligand complexes (Medek, A., et al. J. American Chemical Society, 2000. 122(6):1241–1242), identifying sites on these ligands amenable to modification to compound affinity.

VI. High-Throughput in vitro Fluorescence Polarization Binding Assay

Sensor: Rhodamine-labeled NPXY peptide (final conc.=1–5 nM)

Adaptin: Glutathione-S-transferase/LDLR adaptin PTB domain fusion protein (final conc.=100–200 nM)

Buffer: 10 mM HEPES, 10 mM NaCl, 6 mM magnesium chloride, pH 7.6

1. Add 90 microliters of peptide/adaptin mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

VII. Protocol for High Throughput LDLR Adaptin Domain—Ligand Binding Assay

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.

$^{33}P$ LDLR adaptin PTB domain polypeptide 10×stock: $10^{-8}$–$10^{-6}$M "cold" LDLR adaptin PTB domain supplemented with 200,000–250,000 cpm of labeled LDLR adaptin (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

Ligand: $10^{-7}$–$10^{-5}$ M biotinylated NPVY petide ligand in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-LDLR adaptin PTB domain polypeptide (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 μM biotinylated ligand (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate):

a. Non-specific binding b. Soluble (non-biotinylated ligand) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A commercial drug screen for identifying an agent which alters a function of a human low density lipoprotein receptor (LDLR) adaptin (SEQ ID NO:2 or mutants thereof) by modulating LDLR adaptin—ligand binding, the screen comprising steps:
   combining a phosphotyrosinie binding (PTB) domain of the LDLR adaptin with an NPXY (SEQ ID NO:7) peptide ligand of the PTB domain and an agent under conditions wherein but for the presence of the agent, the PTB domain and peptide ligand engage in a first binding; and
   detecting a second binding of the PTB domain and peptide ligand (in the presence of the agent),
   wherein a difference between the first and second bindings indicates the agent modulates the binding of the PTB domain and the peptide ligand and thereby alters the LDLR adaptin function.

2. A drug screen according to claim 1, wherein the drug screen is a filter binding assay.

3. A drug screen according to claim 1, wherein the drug screen is an NMR-based binding assay.

4. A drug screen according to claim 1, wherein the drug screen is a fluorescence polarization assay.

5. A drug screen according to claim 1, wherein the drug screen is a solid-phase binding assay.

6. A drug screen according to claim 1, wherein the PTB domain comprises residues 48–175 of SEW ID NO:2.

7. A drug screen according to claim 1, 2, or 3, wherein the PTB domain is encoded by an LDLR adaptin cDNA sequence deviating from nucleotides 142–525 of SEQ ID NO:1 by a deviation selected from the group consisting of:
   a) an A insertion at position 432, which introduces a translate frame shift and stop codon at a position corresponding to 170 of SEQ ID NO:2;
   b) a C>T substitution at position 406, which introduces a translate stop codon at a position corresponding to 136 of SEQ ID NO:2;
   c) a C>G substitution at position 239, which introduces a translate A>G substitution at a position corresponding to 80 of SEQ ID NO:2; and
   d) an AA insertion at position 519, which introduces a translate frame shift, a translate V>K substitution at a position corresponding to 174 of SEQ ID NO:2, and a translate S>C substitution at a position corresponding to 175 of SEQ ID NO:2.

8. A drug screen according to claim 1, 2, or 3, wherein the LDLR adaptin comprises the PTB domain.

9. A drug screen according to claim 1, 2, or 3, wherein the LDLR adaptin comprises the PTB domain, and the PTB domain comprises residues 48–175 of SEQ ID NO:2.

10. A drug screen according to claim 1, wherein the LDLR adaptin comprises the PTB domain, and the PTB domain is encoded by an LDLR adaptin cDNA sequence deviating from nucleotides 142–525 of SEQ ID NO:1 by a deviation selected from the group consisting of:
    a) an A insertion at position 432, which introduces a translate frame shift and stop codon at a position corresponding to 170 of SEQ ID NO:2;
    b) a C>T substitution at position 406, which introduces a translate a stop codon a position corresponding to 136 of SEQ ID NO:2;
    c) a C>G substitution at position 239, which introduces a translate A>G substitution at a position corresponding to 80 of SEQ ID NO:2; and
    d) an AA insertion at position 519, which introduces a translate frame shift, a translate V>K substitution at a position corresponding to 174 of SEQ ID NO:2, and a translate S>C substitution at a position corresponding to 175 of SEQ ID NO:2.

11. A drug screen according to claim 1, 2, or 3, wherein the LDLR adaptin comprises the PTB domain, and the LDLR adaptin comprises SEQ ID NO:2.

* * * * *

SEQUENCE LISTING

<160> NUMBER OF SEQ ID NOS: 8

<210> SEQ ID NO 1
<211> LENGTH: 927
<212> TYPE: DNA
<213> ORGANISM: human
<220> FEATURE:
<221> NAME/KEY: CDS
<222> LOCATION: (1)..(924)

<400> SEQUENCE: 1

```
atg gac gcg ctc aag tcg gcg ggg cgg gcg ctg atc cgg agc ccc agc      48
Met Asp Ala Leu Lys Ser Ala Gly Arg Ala Leu Ile Arg Ser Pro Ser
 1               5                  10                  15 ttg gcc aag cag agc tgg ggg ggc ggt ggc cgg cac cgc aag ctg cct      96
Leu Ala Lys Gln Ser Trp Gly Gly Gly Arg His Arg Lys Leu Pro
             20                  25                  30 gag aac tgg aca gac acg cgg gag acg ctg ctg gag ggg atg ctg ttc     144
Glu Asn Trp Thr Asp Thr Arg Glu Thr Leu Leu Glu Gly Met Leu Phe
         35                  40                  45 agc ctc aag tac ctg ggc atg acg cta gtg gag cag ccc aag ggt gag     192
Ser Leu Lys Tyr Leu Gly Met Thr Leu Val Glu Gln Pro Lys Gly Glu
     50                  55                  60 gag ctg tcg gcc gcc gcc atc aag agg atc gtg gct aca gct aag gcc     240
Glu Leu Ser Ala Ala Ala Ile Lys Arg Ile Val Ala Thr Ala Lys Ala
 65                  70                  75                  80 agt ggg aag aag ctg cag aag gtg act ctg aag gtg tcg cca cgg gga     288
Ser Gly Lys Lys Leu Gln Lys Val Thr Leu Lys Val Ser Pro Arg Gly
                 85                  90                  95 att atc ctg aca gac aac ctc acc aac cag ctc att gag aac gtg tcc     336
Ile Ile Leu Thr Asp Asn Leu Thr Asn Gln Leu Ile Glu Asn Val Ser
            100                 105                 110 ata tac agg atc tcc tat tgc aca gca gac aag atg cac gac aag gtg     384
Ile Tyr Arg Ile Ser Tyr Cys Thr Ala Asp Lys Met His Asp Lys Val
        115                 120                 125 ttt gca tac atc gcc cag agc cag cac aac cag agc ctc gag tgc cac     432
Phe Ala Tyr Ile Ala Gln Ser Gln His Asn Gln Ser Leu Glu Cys His
    130                 135                 140 gcc ttc ctc tgc acc aag cgg aag atg gca cag gct gtt acc ctc acc     480
Ala Phe Leu Cys Thr Lys Arg Lys Met Ala Gln Ala Val Thr Leu Thr
145                 150                 155                 160 gta gcc cag gcc ttc aaa gtc gcc ttt gag ttt tgg cag gtg tcc aag     528
Val Ala Gln Ala Phe Lys Val Ala Phe Glu Phe Trp Gln Val Ser Lys
                165                 170                 175
```

```
gaa gag aaa gag aag agg gac aaa gcc agc caa gag gga ggg gac gtc    576
Glu Glu Lys Glu Lys Arg Asp Lys Ala Ser Gln Glu Gly Gly Asp Val
        180                 185                 190 ctg ggg gcc cgc caa gac tgc acc ccc ccc ttg aag agc ttg gtc gcc    624
Leu Gly Ala Arg Gln Asp Cys Thr Pro Pro Leu Lys Ser Leu Val Ala
    195                 200                 205 act ggg aac ctg ctg gac tta gag gag acg gct aag gcc ccg ctg tcc    672
Thr Gly Asn Leu Leu Asp Leu Glu Glu Thr Ala Lys Ala Pro Leu Ser
210                 215                 220 acg gtc agc gcc aac acc acc aac atg gac gag gtg ccg cgg cca caa    720
Thr Val Ser Ala Asn Thr Thr Asn Met Asp Glu Val Pro Arg Pro Gln
225                 230                 235                 240 gcc ttg agt ggc agc agt gtt gtc tgg gag ctg gat gat ggc ctg gat    768
Ala Leu Ser Gly Ser Ser Val Val Trp Glu Leu Asp Asp Gly Leu Asp
                245                 250                 255 gaa gcg ttt tcg agg ctt gcc cag tct cgg aca aac cct cag gtc ctg    816
Glu Ala Phe Ser Arg Leu Ala Gln Ser Arg Thr Asn Pro Gln Val Leu
            260                 265                 270 gac act ggc ctg aca gcc cag gac atg cat tac gcc cag tgc ctc tcg    864
Asp Thr Gly Leu Thr Ala Gln Asp Met His Tyr Ala Gln Cys Leu Ser
        275                 280                 285 cct gtc gac tgg gac aag cct gac agc agc ggc aca gag cag gat gac    912
Pro Val Asp Trp Asp Lys Pro Asp Ser Ser Gly Thr Glu Gln Asp Asp
    290                 295                 300 ctc ttc agc ttc tga                                                927
Leu Phe Ser Phe
305

<210> SEQ ID NO 2
<211> LENGTH: 308
<212> TYPE: PRT
<213> ORGANISM: human

<400> SEQUENCE: 2

Met Asp Ala Leu Lys Ser Ala Gly Arg Ala Leu Ile Arg Ser Pro Ser
 1               5                  10                  15

Leu Ala Lys Gln Ser Trp Gly Gly Gly Arg His Arg Lys Leu Pro
             20                  25                  30

Glu Asn Trp Thr Asp Thr Arg Glu Thr Leu Leu Glu Gly Met Leu Phe
         35                  40                  45

Ser Leu Lys Tyr Leu Gly Met Thr Leu Val Glu Gln Pro Lys Gly Glu
     50                  55                  60

Glu Leu Ser Ala Ala Ala Ile Lys Arg Ile Val Ala Thr Ala Lys Ala
 65                  70                  75                  80

Ser Gly Lys Lys Leu Gln Lys Val Thr Leu Lys Val Ser Pro Arg Gly
                 85                  90                  95

Ile Ile Leu Thr Asp Asn Leu Thr Asn Gln Leu Ile Glu Asn Val Ser
            100                 105                 110

Ile Tyr Arg Ile Ser Tyr Cys Thr Ala Asp Lys Met His Asp Lys Val
        115                 120                 125

Phe Ala Tyr Ile Ala Gln Ser Gln His Asn Gln Ser Leu Glu Cys His
    130                 135                 140

Ala Phe Leu Cys Thr Lys Arg Lys Met Ala Gln Ala Val Thr Leu Thr
145                 150                 155                 160

Val Ala Gln Ala Phe Lys Val Ala Phe Glu Phe Trp Gln Val Ser Lys
                165                 170                 175

Glu Glu Lys Glu Lys Arg Asp Lys Ala Ser Gln Glu Gly Gly Asp Val
            180                 185                 190
```

```
Leu Gly Ala Arg Gln Asp Cys Thr Pro Pro Leu Lys Ser Leu Val Ala
            195                 200                 205

Thr Gly Asn Leu Leu Asp Leu Glu Glu Thr Ala Lys Ala Pro Leu Ser
    210                 215                 220

Thr Val Ser Ala Asn Thr Thr Asn Met Asp Glu Val Pro Arg Pro Gln
225                 230                 235                 240

Ala Leu Ser Gly Ser Ser Val Val Trp Glu Leu Asp Asp Gly Leu Asp
                245                 250                 255

Glu Ala Phe Ser Arg Leu Ala Gln Ser Arg Thr Asn Pro Gln Val Leu
            260                 265                 270

Asp Thr Gly Leu Thr Ala Gln Asp Met His Tyr Ala Gln Cys Leu Ser
        275                 280                 285

Pro Val Asp Trp Asp Lys Pro Asp Ser Ser Gly Thr Glu Gln Asp Asp
    290                 295                 300

Leu Phe Ser Phe
305

<210> SEQ ID NO 3
<211> LENGTH: 2632
<212> TYPE: DNA
<213> ORGANISM: mouse
<220> FEATURE:
<221> NAME/KEY: CDS
<222> LOCATION: (69)..(992)

<400> SEQUENCE: 3
aagttttcct ggaggagttt tggcggcggt agcggcgtca gtggcggcgg cgacaaccgg      60 agcgggcc atg gac gcg ctc aag tcg gcg ggg cgc gcg cta atc cgg agc     110
         Met Asp Ala Leu Lys Ser Ala Gly Arg Ala Leu Ile Arg Ser
         1               5                  10 ccc agt ctg gcc aag cag agc tgg gcg ggc ggc cgg cac cgc aag ttg      158
Pro Ser Leu Ala Lys Gln Ser Trp Ala Gly Gly Arg His Arg Lys Leu
 15                  20                  25                  30 cca gag aac tgg acg gac acg cgg gag aca ctg ctg gag ggc atg gtt      206
Pro Glu Asn Trp Thr Asp Thr Arg Glu Thr Leu Leu Glu Gly Met Val
                 35                  40                  45 ttc agc ctc aag tac ctt ggt atg acg ctg gtg gag cgg ccc aag ggc      254
Phe Ser Leu Lys Tyr Leu Gly Met Thr Leu Val Glu Arg Pro Lys Gly
             50                  55                  60 gag gag ctg tct gca gct gct gtc aag agg atc gta gct aca gcc aag      302
Glu Glu Leu Ser Ala Ala Ala Val Lys Arg Ile Val Ala Thr Ala Lys
         65                  70                  75 gcc agc ggg aag aag ctg cag aag gtg aca ctc aag gtg tca ccc cgg      350
Ala Ser Gly Lys Lys Leu Gln Lys Val Thr Leu Lys Val Ser Pro Arg
 80                  85                  90 ggg atc atc ctg acc gac agc ctc act agc cag ctc atc gag aac gtg      398
Gly Ile Ile Leu Thr Asp Ser Leu Thr Ser Gln Leu Ile Glu Asn Val
 95                 100                 105                 110 tcc att tac agg atc tcc tac tgc act gca gac aag atg cac gac aag      446
Ser Ile Tyr Arg Ile Ser Tyr Cys Thr Ala Asp Lys Met His Asp Lys
                115                 120                 125 gtg ttc gcc tac atc gcc cag agc cag cag aac gag agc ctc gag tgc      494
Val Phe Ala Tyr Ile Ala Gln Ser Gln Gln Asn Glu Ser Leu Glu Cys
            130                 135                 140 cac gcc ttc ctc tgc acc aag cgg aaa gtg gcc caa gcc gtc acc ctg      542
His Ala Phe Leu Cys Thr Lys Arg Lys Val Ala Gln Ala Val Thr Leu
        145                 150                 155 act gta gcc caa gcc ttc aaa gtt gcc ttt gag ttt tgg cag gtg tcc      590
```

```
                 -continued

Thr Val Ala Gln Ala Phe Lys Val Ala Phe Glu Phe Trp Gln Val Ser
    160                 165                 170 aag gaa gag aaa gag aaa agg gag aaa gcc aac cag gaa gga gga gac        638
Lys Glu Glu Lys Glu Lys Arg Glu Lys Ala Asn Gln Glu Gly Gly Asp
175                 180                 185                 190 gtc cca ggg acc cga cgg gac agc acc ccc tca ctg aaa acc ttg gtc        686
Val Pro Gly Thr Arg Arg Asp Ser Thr Pro Ser Leu Lys Thr Leu Val
                195                 200                 205 gct acc ggg aac ctg ctg gat ttg gaa gag gtg gct aag gcc ccg tta        734
Ala Thr Gly Asn Leu Leu Asp Leu Glu Glu Val Ala Lys Ala Pro Leu
            210                 215                 220 tct aca gtc agc gct aat acc aac aac gtg gac gag aca cca cgg cct        782
Ser Thr Val Ser Ala Asn Thr Asn Asn Val Asp Glu Thr Pro Arg Pro
        225                 230                 235 cag gtc ttg ggc aac aac agc gtc gtc tgg gag ctg gat gac ggc ctg        830
Gln Val Leu Gly Asn Asn Ser Val Val Trp Glu Leu Asp Asp Gly Leu
    240                 245                 250 gac gaa gca ttt tca agg ctg gcg cag tcc cgg aca aac cct caa gtc        878
Asp Glu Ala Phe Ser Arg Leu Ala Gln Ser Arg Thr Asn Pro Gln Val
255                 260                 265                 270 ctg gac act gga ctg tca gca cag gac atc cat tat gca cag tgc tta        926
Leu Asp Thr Gly Leu Ser Ala Gln Asp Ile His Tyr Ala Gln Cys Leu
                275                 280                 285 tcg ccc acc gac tgg gac aag cct gac agc agt ggc att gat caa gat        974
Ser Pro Thr Asp Trp Asp Lys Pro Asp Ser Ser Gly Ile Asp Gln Asp
            290                 295                 300 gat gac gtc ttc acc ttc tgaggacccg aggctggcaa tacactactg              1022
Asp Asp Val Phe Thr Phe
            305 gcctagacat gggacggacc ataagccacc agcagcaggc agccaacttc aggagccatc     1082 agctgccttt ggccaggggc gtcagagcct acagattcag gttgcacagt cactcgggga     1142 gagggggaga aagatgcctg cggtatccag ttggtgactc ctggtttatg ctcggaaacc     1202 agtttgattc agtgtgctcat gtgtgtgggg cagggcctgg cctcctggag ccagtgcccc    1262 ctcctgctgt gggcgtcagg acaatgacca aagccgttga tgttcctttt ctctgggcat     1322 cctcactcct gaagcagtaa gagcctgccg ttctttgtgt actggatggg acgtggcttt     1382 caggaaagtt ggggctcctc aagctctgct tcctcggggc cgagtaactg aggctctcag     1442 agaggcagcc cctgaccaaa gacacattta actctgcact taactctcc cgtagtggcc      1502 atggttcgag gtccatgatg gtgctttggg agtagagctt gcctcctgcc ctccctccac     1562 aaggggccc cagtccctga cgtggcccat acagtgctag gacctagtgt accagctgcc      1622 catgactccc agagtcactg caaccatggt gatcacctct gtggctcctg ggagtgcccc     1682 ccacccccac cgccaacaga caaagctggg cctgcttttc tgttttgtct gtttgtcctt     1742 gtgtgtgctc cattttctgc ttccccacaa ttcctgggat gataccaaag cctagcacta     1802 ggctgtggca ggcgattctt gcatccattt tacagataaa gaaactgagg cgacacacgt     1862 gttgagggt ggagttgaga acagaaccca gatctgatac caaagctgcc gtctgtgctg      1922 ccacctccca gcccacgcct ctttctctgt ggctttgttg tcctcccagg aaccaaaact     1982 ccccagctat tttctgacca aaatgtgttt cataacaaac catctggtgc cttttcacac     2042 agcgctggcg caggccgcca tgccctgcta gctgctatgc cgctgacttc tgggcagatg     2102 tgttttgaag tctgttaatt ccatgggtga acggtatct cactctagaa acatcttgct      2162 gtccttttct gacctgcagc cgtagtggtc cctcgaccct agctggtggt cggggcggtc     2222
```

```
cagtggtgag cttctcttaa tctctttcct cccttcgctg gtcccgtggg ctctggcatc   2282
ctgaatctca gccaaactaa caacatcttt ccatcgcttg tgaaagctgg tctcagtgtc   2342
cccaggaaaa cacacttttc ctgagtggct gagtcggacc cttgccttgg gggttggggg   2402
gcacttggag aattcttgct agaataaagg ttgccagctc cctttccctg ccagctcca   2462 aggcccctgc tccttagccc aagtggccag ggtacgggcg cgaggggac tgtgtggtgt   2522 tgggtgatgc tgtagtcttg cttcctgtgc ctgctgccaa tgctgctgtg tgaagctgga   2582
aaggcagttc tgagcaggaa acaataaatg ttcccttct gagtgtgagc              2632
```

<210> SEQ ID NO 4
<211> LENGTH: 308
<212> TYPE: PRT
<213> ORGANISM: mouse

<400> SEQUENCE: 4

```
Met Asp Ala Leu Lys Ser Ala Gly Arg Ala Leu Ile Arg Ser Pro Ser
 1               5                  10                  15

Leu Ala Lys Gln Ser Trp Ala Gly Gly Arg His Arg Lys Leu Pro Glu
            20                  25                  30

Asn Trp Thr Asp Thr Arg Glu Thr Leu Leu Glu Gly Met Val Phe Ser
        35                  40                  45

Leu Lys Tyr Leu Gly Met Thr Leu Val Glu Arg Pro Lys Gly Glu Glu
    50                  55                  60

Leu Ser Ala Ala Val Lys Arg Ile Val Ala Thr Ala Lys Ala Ser
 65                  70                  75                  80

Gly Lys Lys Leu Gln Lys Val Thr Leu Lys Val Ser Pro Arg Gly Ile
                85                  90                  95

Ile Leu Thr Asp Ser Leu Thr Ser Gln Leu Ile Glu Asn Val Ser Ile
            100                 105                 110

Tyr Arg Ile Ser Tyr Cys Thr Ala Asp Lys Met His Asp Lys Val Phe
        115                 120                 125

Ala Tyr Ile Ala Gln Ser Gln Gln Asn Glu Ser Leu Glu Cys His Ala
    130                 135                 140

Phe Leu Cys Thr Lys Arg Lys Val Ala Gln Ala Val Thr Leu Thr Val
145                 150                 155                 160

Ala Gln Ala Phe Lys Val Ala Phe Glu Phe Trp Gln Val Ser Lys Glu
                165                 170                 175

Glu Lys Glu Lys Arg Glu Lys Ala Asn Gln Glu Gly Gly Asp Val Pro
            180                 185                 190

Gly Thr Arg Arg Asp Ser Thr Pro Ser Leu Lys Thr Leu Val Ala Thr
        195                 200                 205

Gly Asn Leu Leu Asp Leu Glu Glu Val Ala Lys Ala Pro Leu Ser Thr
    210                 215                 220

Val Ser Ala Asn Thr Asn Val Asp Glu Thr Pro Arg Pro Gln Val
225                 230                 235                 240

Leu Gly Asn Asn Ser Val Val Trp Glu Leu Asp Asp Gly Leu Asp Glu
                245                 250                 255

Ala Phe Ser Arg Leu Ala Gln Ser Arg Thr Asn Pro Gln Val Leu Asp
            260                 265                 270

Thr Gly Leu Ser Ala Gln Asp Ile His Tyr Ala Gln Cys Leu Ser Pro
        275                 280                 285

Thr Asp Trp Asp Lys Pro Asp Ser Ser Gly Ile Asp Gln Asp Asp
    290                 295                 300
```

```
Val Phe Thr Phe
305

<210> SEQ ID NO 5
<211> LENGTH: 927
<212> TYPE: DNA
<213> ORGANISM: Xenopus laevis
<220> FEATURE:
<221> NAME/KEY: CDS
<222> LOCATION: (1)..(924)

<400> SEQUENCE: 5 atg gat gcg ctt aag tct gct ggg agg gcg atc atc agg agt ccg agc      48
Met Asp Ala Leu Lys Ser Ala Gly Arg Ala Ile Ile Arg Ser Pro Ser
  1               5                  10                  15 att gcc aag cag agc tgg gga gga ggc aag cac aag aaa cta cca gaa      96
Ile Ala Lys Gln Ser Trp Gly Gly Gly Lys His Lys Lys Leu Pro Glu
             20                  25                  30 aac tgg act gat acc agg gaa aca ctc tta gaa gga atg tta ttc cat     144
Asn Trp Thr Asp Thr Arg Glu Thr Leu Leu Glu Gly Met Leu Phe His
         35                  40                  45 ttg aaa tat ttg ggc atg aca ttg gtg gaa caa cca aaa ggg gaa gag     192
Leu Lys Tyr Leu Gly Met Thr Leu Val Glu Gln Pro Lys Gly Glu Glu
     50                  55                  60 ctg tct gca act gca gtg aaa aga att gtg gca act gca aaa gca agt     240
Leu Ser Ala Thr Ala Val Lys Arg Ile Val Ala Thr Ala Lys Ala Ser
 65                  70                  75                  80 ggg aag aaa ctg cag aaa gtt ctt ctg aaa gta tca cca cgg ggc atc     288
Gly Lys Lys Leu Gln Lys Val Leu Leu Lys Val Ser Pro Arg Gly Ile
                 85                  90                  95 att cta cat gac cgc gca acc aac caa cta att gag aat gtt tca atc     336
Ile Leu His Asp Arg Ala Thr Asn Gln Leu Ile Glu Asn Val Ser Ile
            100                 105                 110 tac agg ata tcc tat tgc aca gct gat aaa atg cat gac aaa gtt ttt     384
Tyr Arg Ile Ser Tyr Cys Thr Ala Asp Lys Met His Asp Lys Val Phe
        115                 120                 125 gcc tac att gct cag agc cag cag aat gaa acc ttg gaa tgc cat gca     432
Ala Tyr Ile Ala Gln Ser Gln Gln Asn Glu Thr Leu Glu Cys His Ala
    130                 135                 140 ttt ctt tgc aca aag agg aaa atg gca caa gca gtc aca tta acg gtg     480
Phe Leu Cys Thr Lys Arg Lys Met Ala Gln Ala Val Thr Leu Thr Val
145                 150                 155                 160 gct cag gct ttc aag gta gcg ttt gag ttt tgg caa gta tcc cga gag     528
Ala Gln Ala Phe Lys Val Ala Phe Glu Phe Trp Gln Val Ser Arg Glu
                165                 170                 175 aaa agg aaa aga gag agt ctg gtt cac atg gag aag ggg caa gta gtt     576
Lys Arg Lys Arg Glu Ser Leu Val His Met Glu Lys Gly Gln Val Val
            180                 185                 190 ctc agt ctg atg gct cct cga gta tca cca gcc tta aag cat cag cat     624
Leu Ser Leu Met Ala Pro Arg Val Ser Pro Ala Leu Lys His Gln His
        195                 200                 205 ctg caa acc ttt tgg att ttg gaa gac tgt acc aaa gct ttt gat gtg     672
Leu Gln Thr Phe Trp Ile Leu Glu Asp Cys Thr Lys Ala Phe Asp Val
    210                 215                 220 tta aat gcc agt gac aat cat att gaa gag gta tta agg caa aat gca     720
Leu Asn Ala Ser Asp Asn His Ile Glu Glu Val Leu Arg Gln Asn Ala
225                 230                 235                 240 tcc aat gaa aac aac aat ata gtg tgg gaa ctg gat gat gga ctg gat     768
Ser Asn Glu Asn Asn Asn Ile Val Trp Glu Leu Asp Asp Gly Leu Asp
                245                 250                 255 gag gca ttt gca aga ctt gca gaa tcc aga aca aac cct caa gtc ctg     816
Glu Ala Phe Ala Arg Leu Ala Glu Ser Arg Thr Asn Pro Gln Val Leu
```

| | | | | | | | | | | | |
|---|---|---|---|---|---|---|---|---|---|---|---|
| Glu | Ala | Phe | Ala | Arg | Leu | Ala | Glu | Ser | Arg | Thr | Asn | Pro | Gln | Val | Leu |
| | | | 260 | | | | 265 | | | | 270 | | | | |

```
gat att gga ttg act gca aat gac ctt cag tct gaa gag tgc ttg tct      864
Asp Ile Gly Leu Thr Ala Asn Asp Leu Gln Ser Glu Glu Cys Leu Ser
        275                 280                 285 cct acc agc tgg gat aaa ctg gag ttg aac cct gca gaa gca gat gaa      912
Pro Thr Ser Trp Asp Lys Leu Glu Leu Asn Pro Ala Glu Ala Asp Glu
290                 295                 300 cta ttt atg ttc tga                                                  927
Leu Phe Met Phe
305
```

<210> SEQ ID NO 6
<211> LENGTH: 308
<212> TYPE: PRT
<213> ORGANISM: Xenopus laevis

<400> SEQUENCE: 6

Met Asp Ala Leu Lys Ser Ala Gly Arg Ala Ile Ile Arg Ser Pro Ser
1               5                   10                  15

Ile Ala Lys Gln Ser Trp Gly Gly Lys His Lys Lys Leu Pro Glu
            20                  25                  30

Asn Trp Thr Asp Thr Arg Glu Thr Leu Leu Glu Gly Met Leu Phe His
        35                  40                  45

Leu Lys Tyr Leu Gly Met Thr Leu Val Glu Gln Pro Lys Gly Glu Glu
    50                  55                  60

Leu Ser Ala Thr Ala Val Lys Arg Ile Val Ala Thr Ala Lys Ala Ser
65                  70                  75                  80

Gly Lys Lys Leu Gln Lys Val Leu Leu Lys Val Ser Pro Arg Gly Ile
                85                  90                  95

Ile Leu His Asp Arg Ala Thr Asn Gln Leu Ile Glu Asn Val Ser Ile
            100                 105                 110

Tyr Arg Ile Ser Tyr Cys Thr Ala Asp Lys Met His Asp Lys Val Phe
        115                 120                 125

Ala Tyr Ile Ala Gln Ser Gln Gln Asn Glu Thr Leu Glu Cys His Ala
    130                 135                 140

Phe Leu Cys Thr Lys Arg Lys Met Ala Gln Ala Val Thr Leu Thr Val
145                 150                 155                 160

Ala Gln Ala Phe Lys Val Ala Phe Glu Phe Trp Gln Val Ser Arg Glu
                165                 170                 175

Lys Arg Lys Arg Glu Ser Leu Val His Met Glu Lys Gly Gln Val Val
            180                 185                 190

Leu Ser Leu Met Ala Pro Arg Val Ser Pro Ala Leu Lys His Gln His
        195                 200                 205

Leu Gln Thr Phe Trp Ile Leu Glu Asp Cys Thr Lys Ala Phe Asp Val
    210                 215                 220

Leu Asn Ala Ser Asp Asn His Ile Glu Glu Val Leu Arg Gln Asn Ala
225                 230                 235                 240

Ser Asn Glu Asn Asn Ile Val Trp Glu Leu Asp Asp Gly Leu Asp
                245                 250                 255

Glu Ala Phe Ala Arg Leu Ala Glu Ser Arg Thr Asn Pro Gln Val Leu
            260                 265                 270

Asp Ile Gly Leu Thr Ala Asn Asp Leu Gln Ser Glu Glu Cys Leu Ser
        275                 280                 285

Pro Thr Ser Trp Asp Lys Leu Glu Leu Asn Pro Ala Glu Ala Asp Glu
    290                 295                 300

```
Leu Phe Met Phe
305

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence
<221> NAME/KEY: VARIANT
<222> LOCATION: (3)
<223> OTHER INFORMATION: Xaa signifies any amino acid

<400> SEQUENCE: 7

Asn Pro Xaa Tyr
  1

<210> SEQ ID NO 8
<211> LENGTH: 860
<212> TYPE: PRT
<213> ORGANISM: human

<400> SEQUENCE: 8

Met Gly Pro Trp Gly Trp Lys Leu Arg Trp Thr Val Ala Leu Leu Leu
 1               5                  10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270
```

```
Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
    515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685
```

-continued

```
Pro His Ser Pro Lys Phe Thr Cys Ala Cys Pro Asp Gly Met Leu Leu
    690             695             700

Ala Arg Asp Met Arg Ser Cys Leu Thr Glu Ala Glu Ala Ala Val Ala
705             710             715             720

Thr Gln Glu Thr Ser Thr Val Arg Leu Lys Val Ser Ser Thr Ala Val
            725             730             735

Arg Thr Gln His Thr Thr Thr Arg Pro Val Pro Asp Thr Ser Arg Leu
            740             745             750

Pro Gly Ala Thr Pro Gly Leu Thr Thr Val Glu Ile Val Thr Met Ser
        755             760             765

His Gln Ala Leu Gly Asp Val Ala Gly Arg Gly Asn Glu Lys Lys Pro
    770             775             780

Ser Ser Val Arg Ala Leu Ser Ile Val Leu Pro Ile Val Leu Leu Val
785             790             795             800

Phe Leu Cys Leu Gly Val Phe Leu Leu Trp Lys Asn Trp Arg Leu Lys
            805             810             815

Asn Ile Asn Ser Ile Asn Phe Asp Asn Pro Val Tyr Gln Lys Thr Thr
            820             825             830

Glu Asp Glu Val His Ile Cys His Asn Gln Asp Gly Tyr Ser Tyr Pro
        835             840             845

Ser Arg Gln Met Val Ser Leu Glu Asp Asp Val Ala
    850             855             860
```